(12) United States Patent  
Lin et al.

(10) Patent No.: US 8,896,834 B2  
(45) Date of Patent: Nov. 25, 2014

(54) OPTICAL GAS SENSOR

(75) Inventors: Jing-Yuan Lin, New Taipei (TW); Shang-Chian Su, New Taipei (TW)

(73) Assignee: Industrial Technology Research Institute, Hsinchu (TW)

( * ) Notice: Subject to any disclaimer, the term of this patent is extended or adjusted under 35 U.S.C. 154(b) by 0 days.

(21) Appl. No.: 13/553,750

(22) Filed: Jul. 19, 2012

(65) Prior Publication Data

US 2013/0258345 A1    Oct. 3, 2013

(30) Foreign Application Priority Data

Mar. 28, 2012    (TW) .............................. 101110781 A

(51) Int. Cl.
- *G01N 21/00*    (2006.01)
- *G01J 5/02*    (2006.01)
- *B05D 3/06*    (2006.01)

(52) U.S. Cl.
CPC .... *G01J 5/02* (2013.01); *B05D 3/06* (2013.01)
USPC ........................................................ 356/437

(58) Field of Classification Search
USPC ........ 356/437; 250/343; 204/288; 427/8, 123
See application file for complete search history.

(56) References Cited

U.S. PATENT DOCUMENTS

| | | | |
|---|---|---|---|
| 5,444,249 A | 8/1995 | Wong | |
| 5,492,718 A * | 2/1996 | O'Neill et al. | 427/8 |
| 5,747,808 A | 5/1998 | Wong | |
| 5,834,777 A * | 11/1998 | Wong | 250/343 |
| 6,469,303 B1 | 10/2002 | Sun et al. | |
| 6,989,549 B2 | 1/2006 | Diekmann et al. | |
| 7,157,054 B2 | 1/2007 | Toyoda et al. | |
| 7,244,939 B2 | 7/2007 | Stuttard | |
| 7,378,656 B2 | 5/2008 | Ichihara et al. | |
| 7,488,942 B2 * | 2/2009 | Hopkins et al. | 250/343 |
| 7,495,300 B2 | 2/2009 | Gardner et al. | |
| 8,006,553 B2 | 8/2011 | Abe et al. | |
| 2004/0026239 A1 * | 2/2004 | Kishimi et al. | 204/288 |
| 2004/0197467 A1 * | 10/2004 | Nakata et al. | 427/123 |
| 2007/0090293 A1 | 4/2007 | Ichihara et al. | |
| 2012/0161253 A1 | 6/2012 | Hsieh et al. | |

FOREIGN PATENT DOCUMENTS

| | | |
|---|---|---|
| CN | 1705871 | 12/2005 |
| JP | 2006300738 | 11/2006 |
| TW | 200415680 | 8/2004 |

OTHER PUBLICATIONS

Lai et al, "MEMS integrated narrow band infrared emitter and detector for infrared gas sensor", Journal of Physics: Conference Series, 2011, pp. 1~5, vol. 276.
Jun et al, "Miniature low-power IR monitor for methane detection", Measurement, Jun. 2011, pp. 823~831, vol. 44, No. 5.

(Continued)

*Primary Examiner* — Tarifur Chowdhury
*Assistant Examiner* — Jamil Ahmed
(74) *Attorney, Agent, or Firm* — Jianq Chyun IP Office

(57) ABSTRACT

In the optical gas sensor of the application, a three-dimensional reaction chamber structure is used to replace the traditional simple structure, so that the performance of the gas sensor can be enhanced in a wafer-level size. Besides, a light source, a reaction chamber and a light detector are integrated into one wafer in an exemplary embodiment, so as to achieve the wafer-level integration. In addition, the optical gas sensor can detect various gases simultaneously and has wide application in fields such as home environment monitoring, industrial safety, and disease diagnosis and treatment.

11 Claims, 17 Drawing Sheets

(56) References Cited

OTHER PUBLICATIONS

Hwang et al., "Development of Micro-Heaters with Optimized Temperature Compensation Design for Gas Sensors", Mar. 1, 2011, Sensors, pp. 2580~2591, vol. 11.

Mayrwoger et al., "Gas Monitoring with a Fabry-Perot Based Bolometer: Cross-Sensitivity to Water Vapor", Procedia Engineering, Oct. 23, 2010, p. 1~1, vol. 5.

Mayrwoger et al., "CO2 monitoring using a simple Fabry-Perot-based germanium bolometer", Sensors and Actuators B: Chemical, Jun. 20, 2011, pp. 245~250, vol. 154, No. 2.

Spannhake et al, "SnO2:Sb—A new material for high-temperature MEMS heater applications: Performance and limitations", Sensors and Actuators B: Chemical, Jan. 13, 2007, pp. 421~428, vol. 124, No. 2.

"Office Action of Taiwan Counterpart Application", issued on Apr. 22, 2014, pp. 1-5, in which the listed reference was cited.

\* cited by examiner

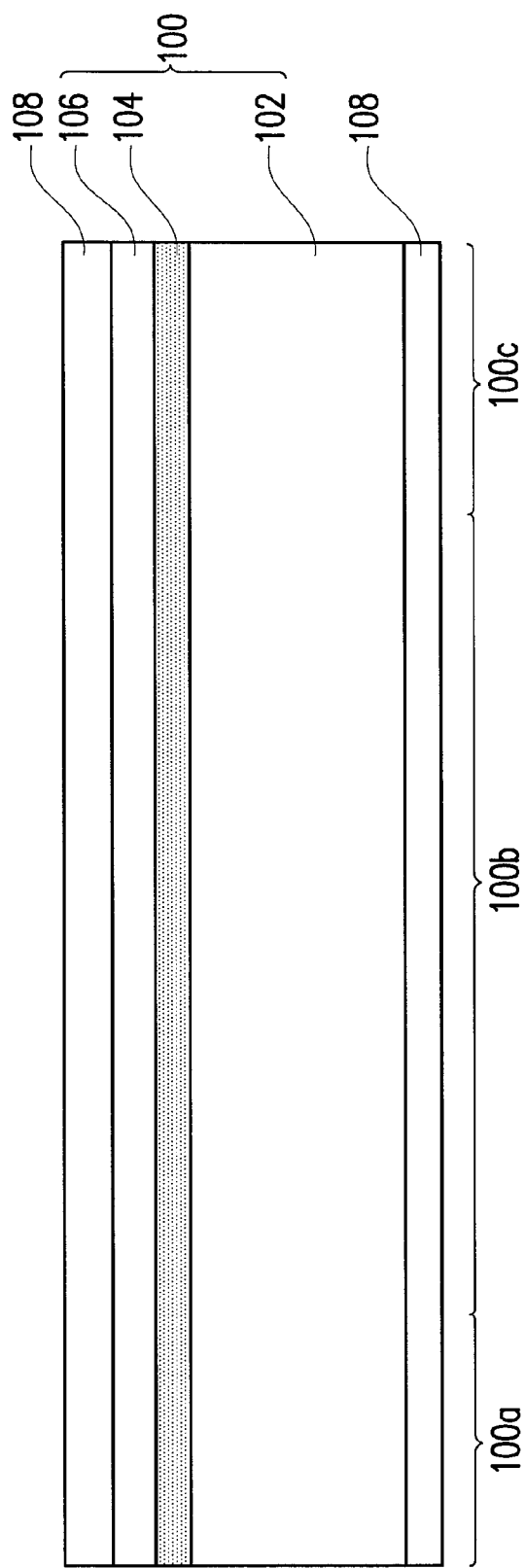

OPTICAL GAS SENSOR

CROSS-REFERENCE TO RELATED APPLICATION

This application claims the priority benefit of Taiwan application serial no. 101110781, filed on Mar. 28, 2012. The entirety of the above-mentioned patent application is hereby incorporated by reference herein and made a part of this specification.

BACKGROUND

1. Technical Field

The technical field relates to an optical gas sensor.

2. Background

A gas sensor is a device having important meaning for human life and health. Demands for gas detection are wide, for example, in the fields of home environment monitoring, industrial safety, and disease diagnosis and treatment. Moreover, due to the requirements for industrial safety and environmental regulations, the gas sensor plays an important role.

Gas sensors can be divided into different categories by the kinds of gases to be detected or by the working principles. The working principles of the gas sensors have electrochemistry, solid electrolyte, optics, oxide semiconductor etc. The first-generation gas sensor is a liquid electrochemical gas sensor. Such liquid electrochemical gas sensor has strong corrosion of the electrolyte solution, large volume and need for regular maintenance. Since the solid-state gas sensor can be miniaturized, it is in mass production to replace the liquid electrochemical gas sensor. However, the solid-state gas sensor requires a micro-heater to raise its temperature and thereby sensitivity, the sensing material thereof has specificity for the gas to be detected, and the solid-state gas sensor needs to contact the gas to be able to use. Therefore, in the use of the solid state gas sensor, attention should be paid to flashover caused by the high temperature, detection failure due to contaminated sensing material etc.

The current optical gas sensor has a complicated optical system and cannot be easily miniaturized and fabricated in batch production, so that it is not affordable in the market. Therefore, how to simplify and miniaturize the optical gas sensor to fabricate one integrated platform at a wafer level has been drawn highly attention in the industry.

SUMMARY

One of exemplary embodiments provides an optical gas sensor, comprising a substrate, a light source disposed in the substrate, at least one light detector disposed in the substrate, and at least one reaction chamber structure disposed in the substrate and connected between the light source and the light detector. The distance from the light source to the light detector is d, and the shortest travel path of a light from the light source to the light detector through the reaction chamber structure is greater than d.

Several exemplary embodiments accompanied with figures are described in detail below to further describe the disclosure in details.

BRIEF DESCRIPTION OF THE DRAWINGS

The accompanying drawings are included to provide further understanding, and are incorporated in and constitute a part of this specification. The drawings illustrate exemplary embodiments and, together with the description, serve to explain the principles.

FIGS. 2A to 2H are cross-sectional schematic diagrams illustrating a method of forming an optical gas sensor according to the first embodiment.

FIG. 2H-1 is cross-sectional schematic diagram illustrating an optical gas sensor according to the first embodiment.

DETAILED DESCRIPTION OF DISCLOSED EMBODIMENTS

Figure 1A:
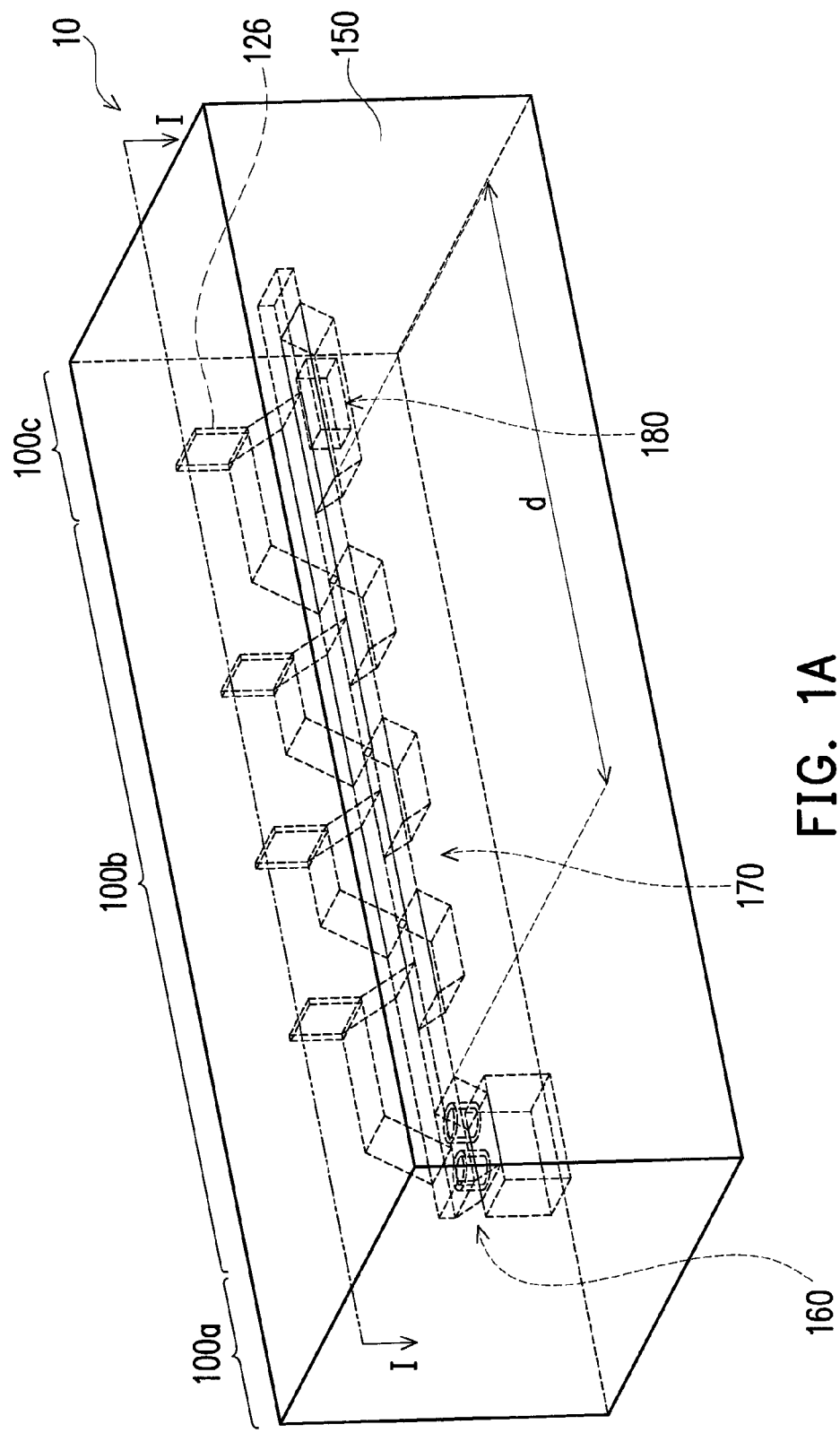
FIG. 1A is a three-dimensional schematic diagram illustrating an optical gas sensor according to the first embodiment.

The exemplary embodiments may be understood more readily by reference to the following detailed description and the accompanying drawings. The exemplary embodiments may, however, be embodied in many different forms and should not be construed as being limited to the embodiments set forth herein. In the drawings, sizes and relative sizes of elements may be exaggerated for clarity.

Spatially relative terms, such as "on", "below", "top surface", "bottom surface", "upper", "lower" and the like, may be used herein for ease of description to describe one element's relationship to another element(s) as illustrated in the figures. People skilled in the art should appreciate that the spatially relative terms are intended to encompass different orientations of the device in use or operation in addition to the orientation depicted in the figures. For example, if the device in the figures is turned over, elements described as "below" other elements would then be oriented "on" the other elements. Thus, the term "below" can encompass both an orientation of "on" and "below". The device may be otherwise oriented (rotated 90 degrees or at other orientations) and the spatially relative descriptors used herein may be interpreted accordingly. In other words, the on-and-below relationship herein can be interpreted as a right-and-left relationship or a back-and-forth relationship, and is not limited by the orientation in the figures.

First Embodiment

Figure 1B:
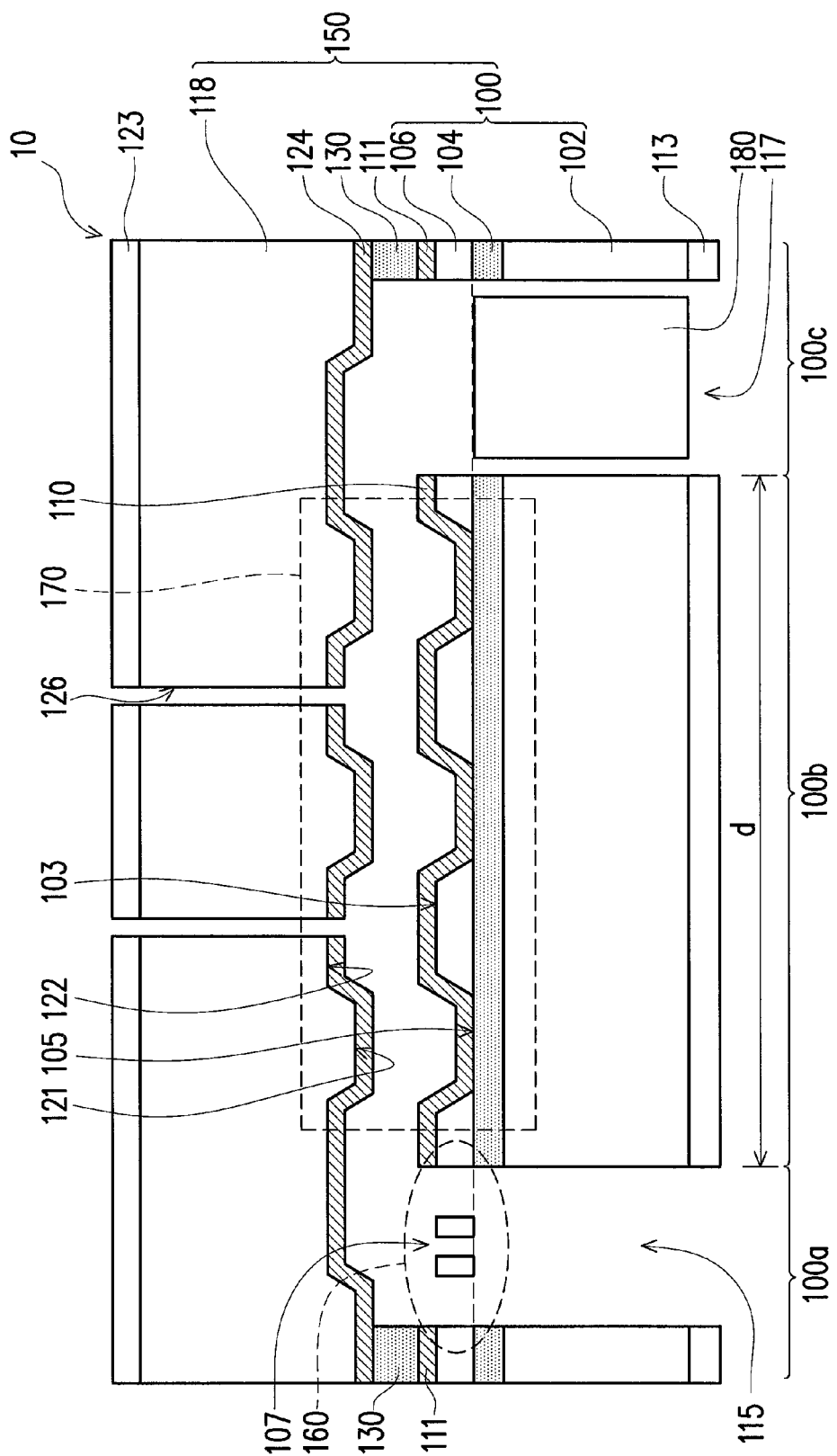
FIG. 1B is a cross-sectional schematic diagram taken along line I-I of FIG. 1A.

FIG. 1A is a three-dimensional schematic diagram illustrating an optical gas sensor according to the first embodiment. FIG. 1B is a cross-sectional schematic diagram taken along line I-I of FIG. 1A.

Referring to FIGS. 1A and 1B, the optical gas sensor 10 of the first embodiment includes a substrate 150, a light source 160, a reaction chamber structure 170 and a light detector 180. The substrate 150 includes a silicon-on-insulator (SOI) substrate, a silicon substrate, a metal substrate, a plastic substrate or a combination thereof. In an embodiment, the substrate 150 is composed of a first sub-substrate 100 and a second sub-substrate 118, wherein the first sub-substrate 100 is a SOI substrate and the second sub-substrate 118 is a silicon substrate.

The substrate 150 has a first area 100a, a second area 100b and a third area 100c. The second area 100b is disposed between the first area 100a and the third area 100c. In an embodiment, the first area 100a is a light source area, the second area 100b is a reaction chamber area, and the third area 100c is a light detector area.

The light source 160 and the light detector 180 are separately disposed in the substrate 150. Specifically, the light source 160 and the light detector 180 are respectively disposed in the first and third areas 100a and 100c of the first sub-substrate 100.

The reaction chamber structure 170 is disposed in the substrate 150. Specifically, the reaction chamber structure 170 is disposed in the second area 100b of the substrate 150 and connected between the light source 160 and the light detector 180.

In an embodiment, the reaction chamber structure 170 is composed of the first sub-substrate 100 and the second sub-substrate 118. The first sub-substrate 100 has a plurality of convex portions 103 and concave portions 105 disposed alternately, the second sub-substrate 118 has a plurality of convex portions 121 and concave portions 122 disposed alternately. The convex portions 103 of the first sub-substrate 100 correspond to the concave portions 122 of the second sub-substrate 118, and the concave portions 105 of the first sub-substrate 100 correspond to the convex portions 121 of the second sub-substrate 118. Further, metal layers or reflective layers 110 and 124 with high reflectivity are coated on the inner walls of the reaction chamber structure 170. Specifically, the reflective layer 110 is coated on the surfaces of the convex portions 103 and the concave portions 105 of the first sub-substrate 100, and the reflective layer 124 is coated on the surfaces of the convex portions 121 and the concave portions 122 of the second sub-substrate 118. The material of the reflective layers 110 and 124 can be, but is not limited to, gold or silver.

The optical gas sensor 10 of the first embodiment further includes a plurality of gas holes 126 for gas in and out. The gas holes 126 are disposed in the second sub-substrate 118 of the substrate 150 and in communication with the reaction chamber structure 170.

It is noted that in the optical gas sensor 10 of the first embodiment, the distance from the light source 160 to the light detector 180 is d, and the shortest travel path L of a light from the light source 160 to the light detector 180 through the reaction chamber structure 170 is greater than d. As shown in FIG. 1B, the light emitted from the light source 160 is reflected multiple times by the inner walls of the reaction chamber structure 170 and absorbed by the gas and then enters the light detector 180. The gas concentration can be calculated by detecting the light amount entering the light detector 180. Due to the special design of the reaction chamber structure 170, the shortest travel path L of the light is greater than straight-line distance d from the light source 160 to the light detector 180, thereby significantly increasing the waveguide path. Accordingly, the signal identification capability of the optical gas sensor is greatly enhanced even with such limited reaction chamber volume.

The method of forming the optical gas sensor 10 of the first embodiment is illustrated in the following. FIGS. 2A to 2H are cross-sectional schematic diagrams illustrating a method of forming an optical gas sensor according to the first embodiment.

Referring to FIG. 2A, a first sub-substrate 100 is provided. The first sub-substrate 100 can be a SOI substrate including, from bottom to top, a lower silicon layer 102, a buried oxide (BOX) layer 104 and an upper silicon layer 106. The first sub-substrate 100 has a first area 100a, a second area 100b and a third area 100c. The second area 100b is disposed between the first area 100a and the third area 100c. In an embodiment, the first area 100a is a light source area, the second area 100b is a reaction chamber area, and the third area 100c is a light detector area.

An insulating material layer 108 is formed on the top and bottom surfaces of the first sub-substrate 100. Specifically, the insulating material layer 108 is formed on the surfaces of the lower silicon layer 102 and the upper silicon layer 106. The material of the insulating material layer 108 can be, but is not limited to, silicon nitride, and the forming method thereof includes performing a chemical vapour deposition (CVD) process.

Figure 2B:
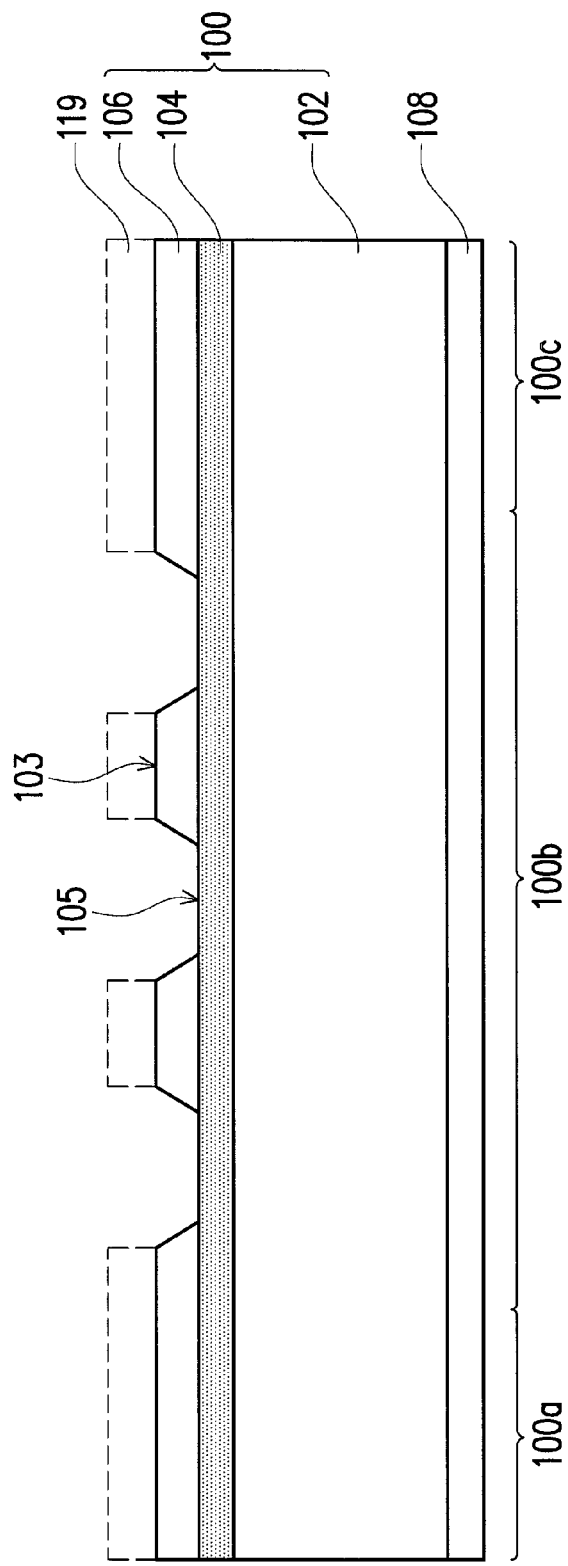

Referring to FIG. 2B, a patterning step is performed to the insulating material layer 108 on the upper silicon layer 106, so as to form an insulating layer 119. The patterning step includes photolithography and etching processes. A portion of the upper silicon layer 106 is removed by using the insulating layer 119 as a mask, so as to form a plurality of convex portions 103 and concave portions 105 disposed alternately in the upper silicon layer 106 in the second area 100b. Each of the convex portions 103 and the concave portions 105 has an incline sidewall, for example. The concave portions 105 expose a portion of the buried oxide layer 104. The insulating layer 119 is removed.

Figure 2C:
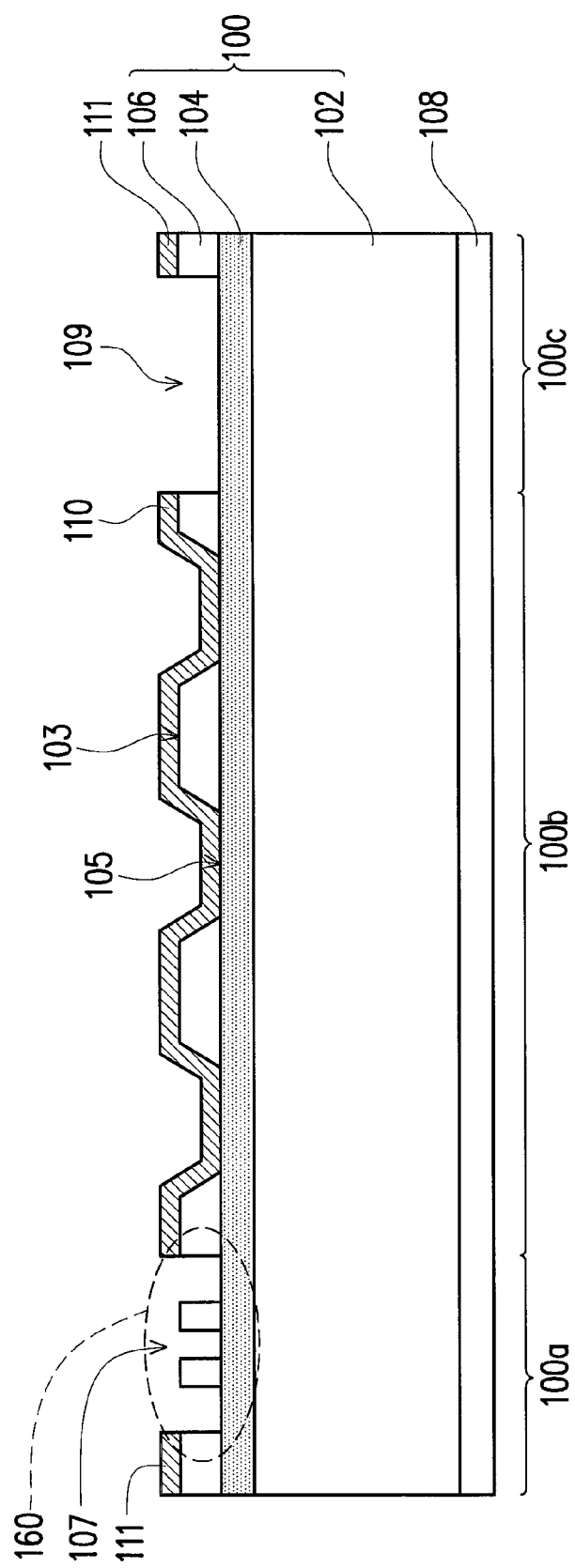

Referring to FIG. 2C, another pattering step is performed to form a plurality of openings 107 in the upper silicon layer 106 in the first area 100a and form an opening 109 in the upper silicon layer 106 in the third area 100c. The patterning step includes photolithography and etching processes. The light source 160 of the embodiment is in the area where the openings 107 are located. The light source 160 has at least one conductive wire, a heat sink or other components (not shown) to emit the infrared light.

A reflective layer 110 made of gold or silver is formed on the surfaces of the convex portions 103 and the concave portions 105 in the second area 100b. Further, during the step of forming the reflective layer 110, two pads 111 are simultaneously formed on the upper silicon layer 106 respectively in the first and third areas 100a and 100c. The method of forming the reflective layer 110 includes forming a patterned photoresist layer and a metal material layer (not shown). The metal material layer can be formed through an evaporation process, for example. A portion of the metal material layer is removed by using the patterned photoresist layer as a sacrificial layer.

It is noted that in the embodiment, the material of the reflective layer 110 is the same as that of the pads 111, but in another embodiment, the material of the reflective layer 110 can be different from that of the pads 111. For example, the reflective layer 110 is made of non-conductive metal with high reflectivity, but the pads 111 are made of conductive metal.

Figure 2D:
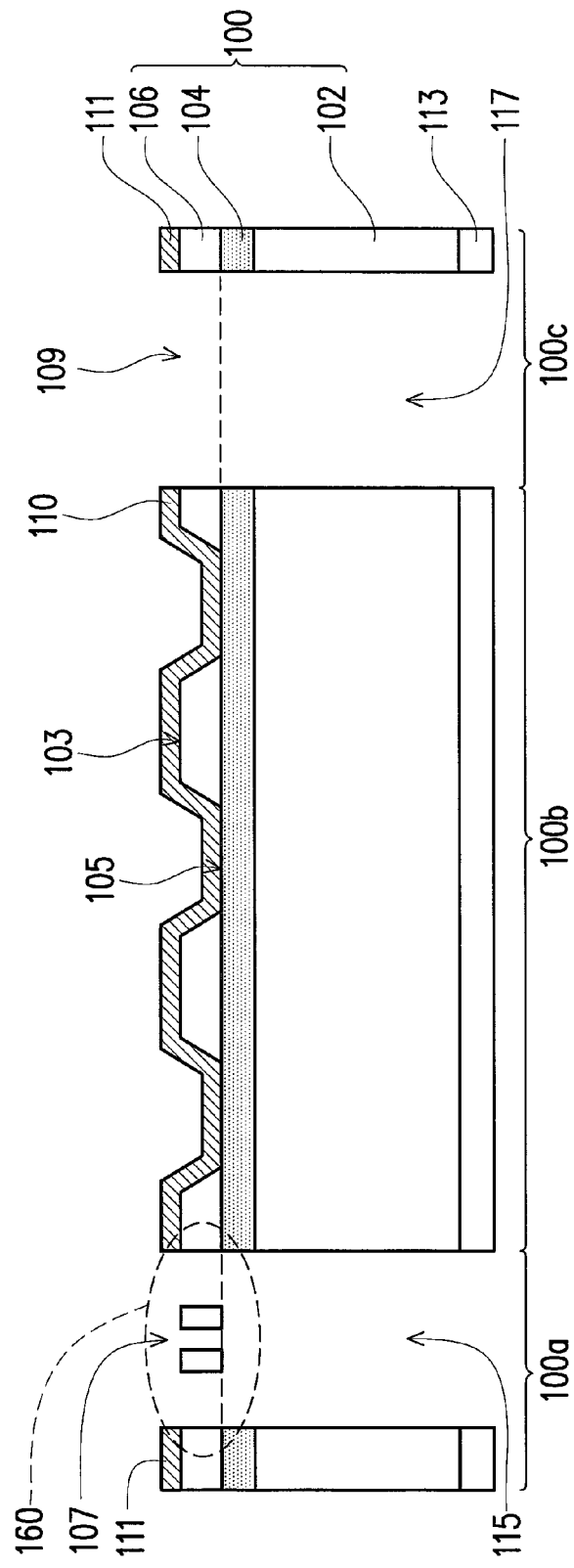

Referring to FIG. 2D, a patterning step is performed to the insulating material layer 108 on the bottom surface of the first sub-substrate 100, so as to form an insulating layer 113. The patterning step includes performing lithography and etching processes. A portion of the lower silicon layer 102 and a portion of the buried oxide layer 104 are removed by using the insulating layer 113 as a mask, so as to form openings 115 and 117 penetrating through the lower silicon layer 102 and the buried oxide layer 104. The opening 115 corresponds to the light source 160 and the opening 117 corresponds to the opening 109. The method of forming the openings 115 and 117 includes performing an etching process.

Figure 7A:
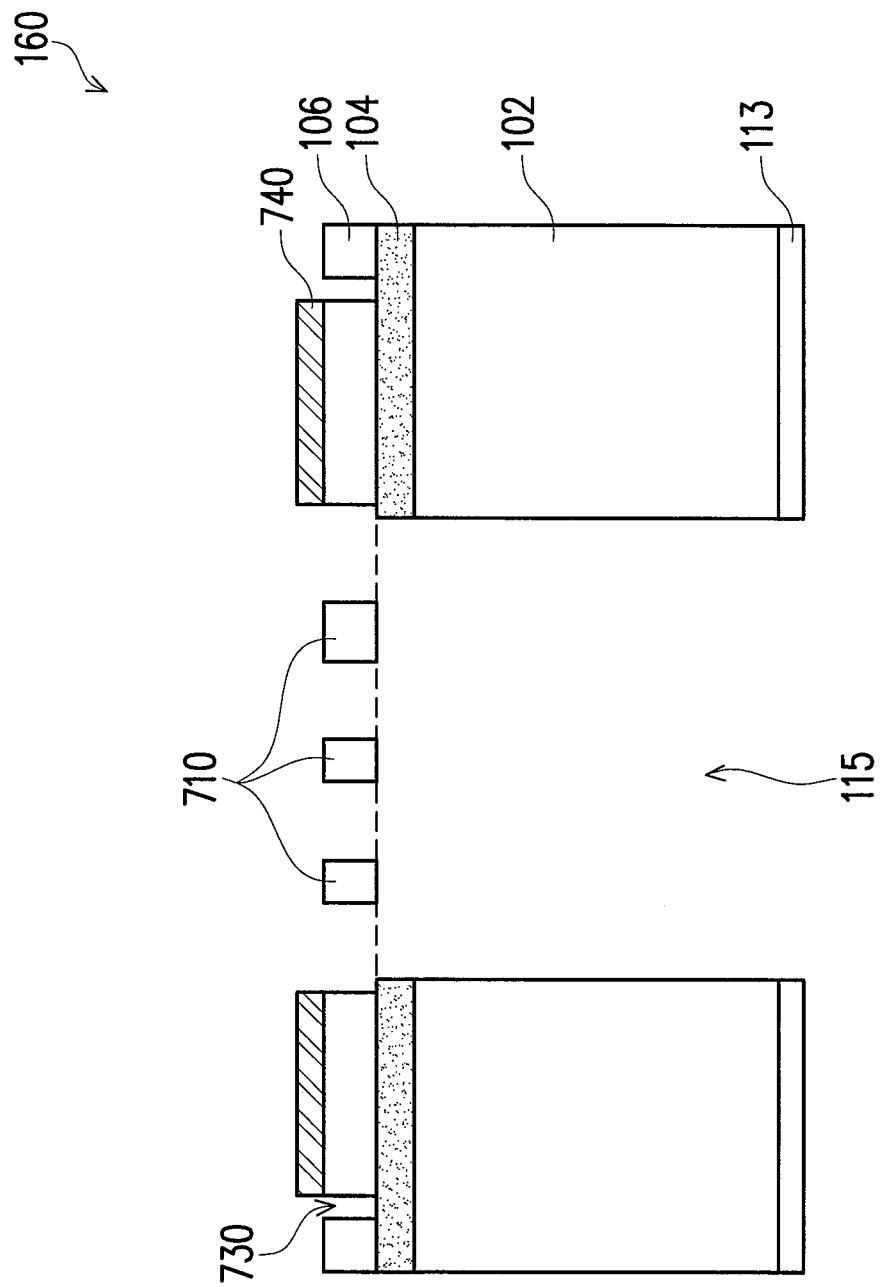
FIG. 7A is a cross-sectional schematic diagram illustrating a light source of an optical gas sensor according to an exemplary embodiment.
Figure 7B:
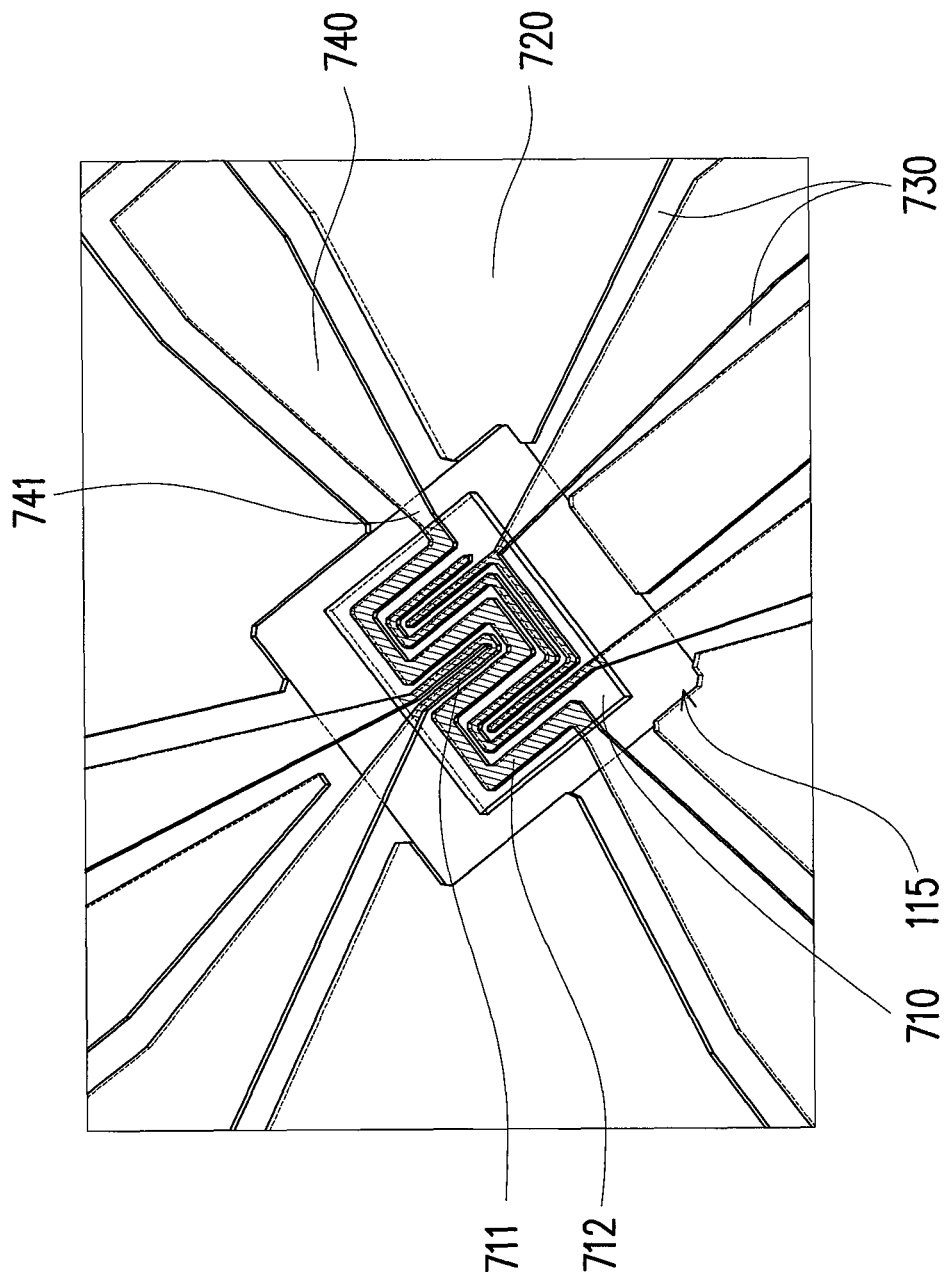
FIG. 7B is a top schematic diagram illustrating a light source of an optical gas sensor according to an exemplary embodiment.

In this embodiment, the light source 160 can be fabricated simultaneously in the previous process steps with reference to FIGS. 7A and 7B. The upper silicon layer 106 of the first sub-substrate 100 is etched to form an integrated circuit region 710, a periphery region 720, a trench 730 and at least one conductive wire 740. The conductive wire 740 includes a connection arm 741 connected to the integrated circuit region 710. The trench 730 is formed around the conductive wire 740 with a depth to the buried oxide layer 104. A gap exists between the integrated circuit region 710 and the periphery region 720, and the connection arm 741 crosses the gap and is connected to the integrated circuit region 710. The lower silicon layer 102 and the buried oxide layer 104 are etched to form the opening 115, and the opening 115 is in communication with the gap. The conductive wire 740 is formed through a metal lift-off process. The integrated circuit region 710 further includes a temperature sensor circuit 711 and a heating circuit 712. A sensing material is coated or printed on the integrated circuit region 710 which is suspended in the opening 115 via the connection arm 741.

Figure 2E:
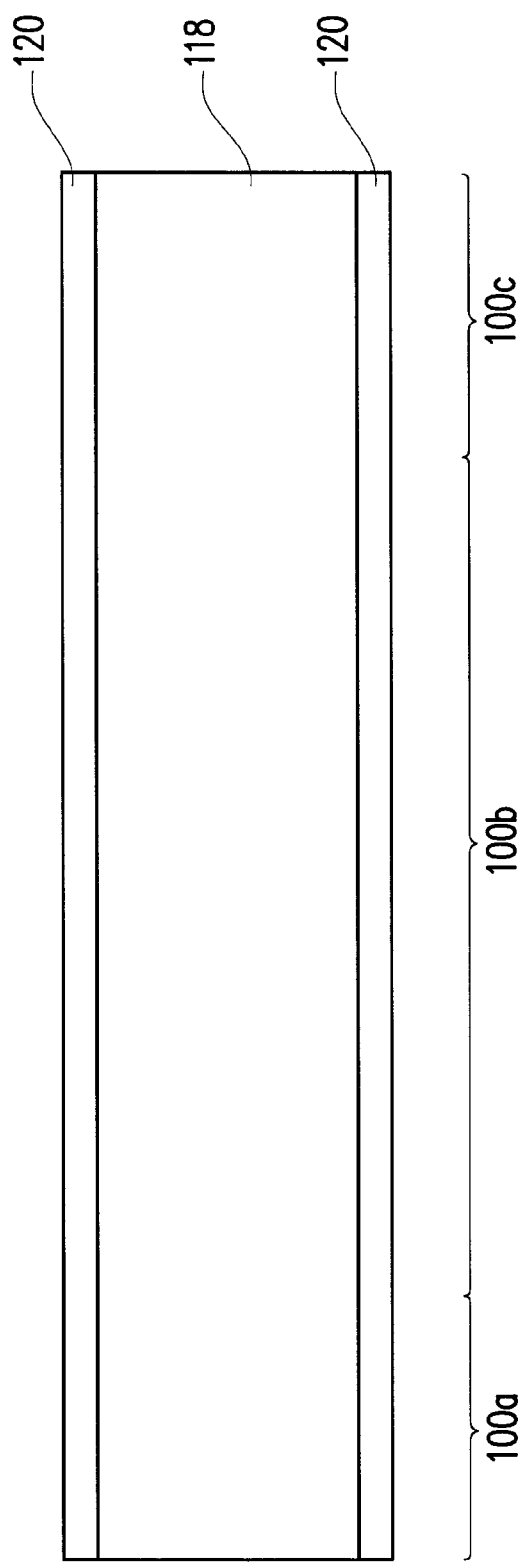

Referring to FIG. 2E, a second sub-substrate 118 is provided. The second sub-substrate 118 can be a silicon substrate. An insulating material layer 120 is formed on the top and bottom surfaces of the second sub-substrate 118. The material of the insulating material layer 120 can be, but is not limited to, silicon nitride, and the forming method thereof includes performing a CVD process.

Figure 2F:
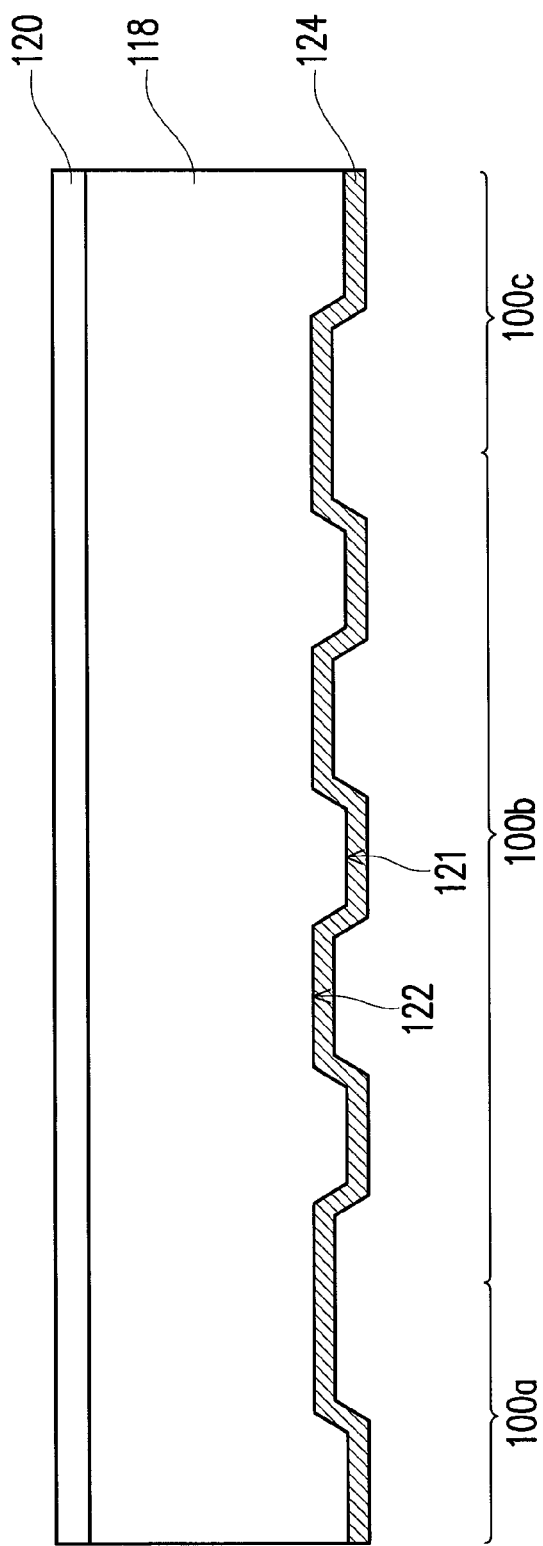

Referring to FIG. 2F, a patterning step is performed to the insulating material layer 120 on the bottom surface of the second sub-substrate 118, so as to form a plurality of convex portions 121 and concave portions 122 disposed alternately in a portion of the second sub-substrate 118. Each of the convex portions 121 and the concave portions 122 has an inclined sidewall, for example. The remaining insulating material layer 120 covers the convex portions 121. The patterning step includes photolithography and etching processes. The remaining insulating material layer 120 is then removed through an etching process.

A reflective layer 124 made of gold or silver is formed on the surfaces of the convex portions 121 and the concave portions 122. The method of forming the reflective layer 124 includes performing an evaporation process. Besides, the material of the reflective layer 110 can be the same or different from that of the reflective layer 124.

Figure 2G:
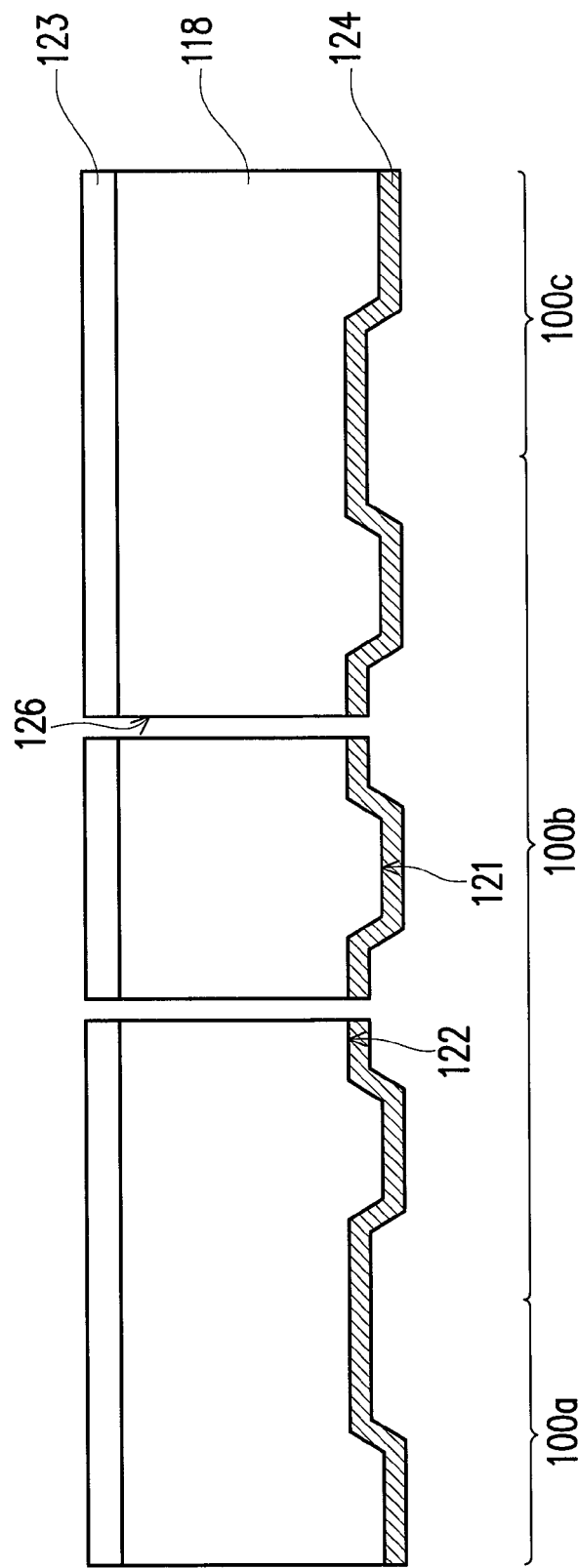

Referring to FIG. 2G, another patterning step is performed to the insulating material layer 120 on the top surface of the second sub-substrate 118, so as to form an insulating layer 123. The patterning step includes photolithography and etching processes. A portion of the second sub-substrate 118 and a portion of the reflective layer 124 are removed by using the insulating layer 123 as a mask, so as to form a plurality of gas holes 126 penetrating through the second sub-substrate 118 and the reflective layer 124. The gas holes 126 allow gas to be detected to pass in and out. The method of forming the gas holes 126 includes performing an etching process.

Figure 2H:
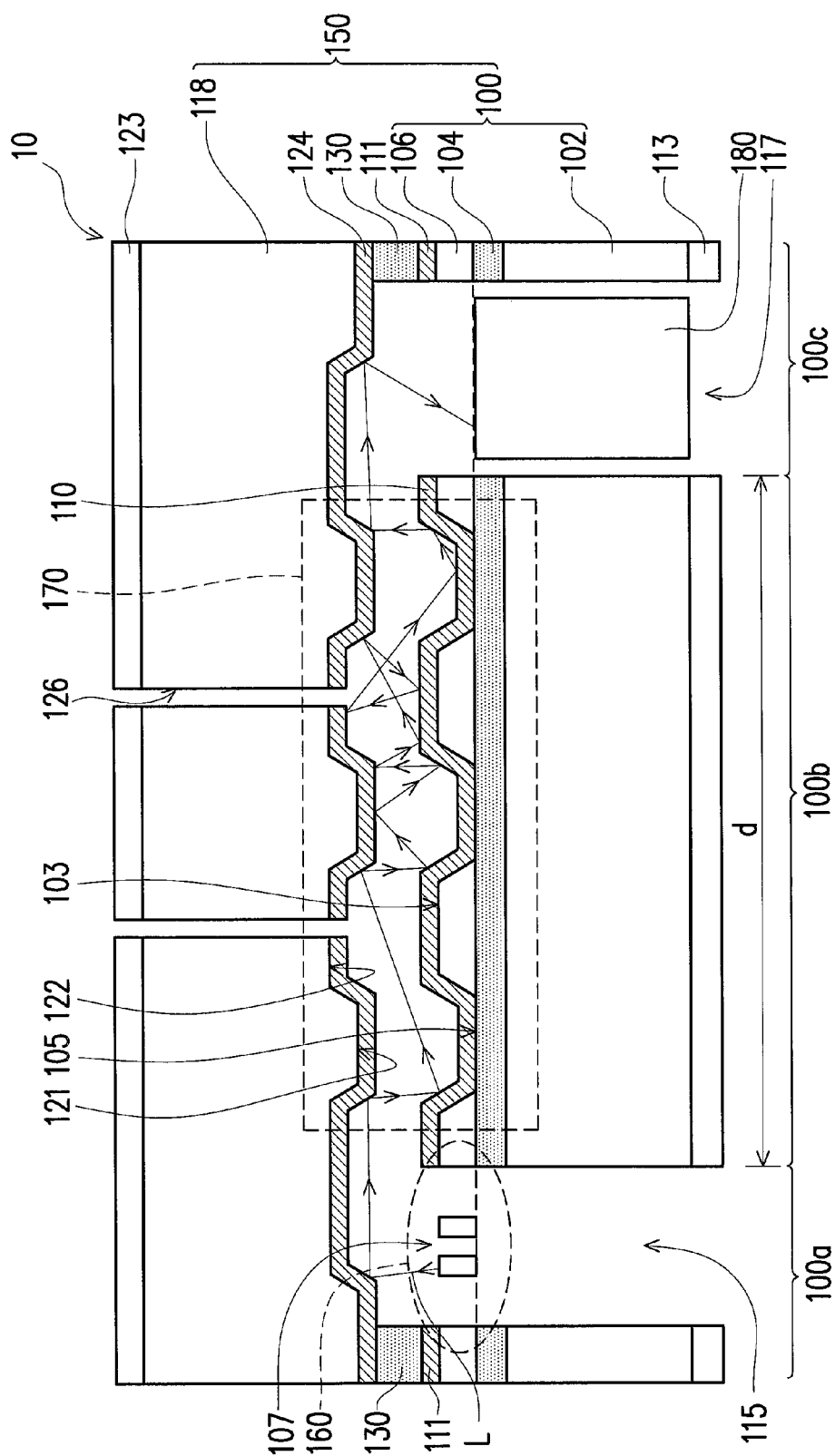
Figures 1, 2H:
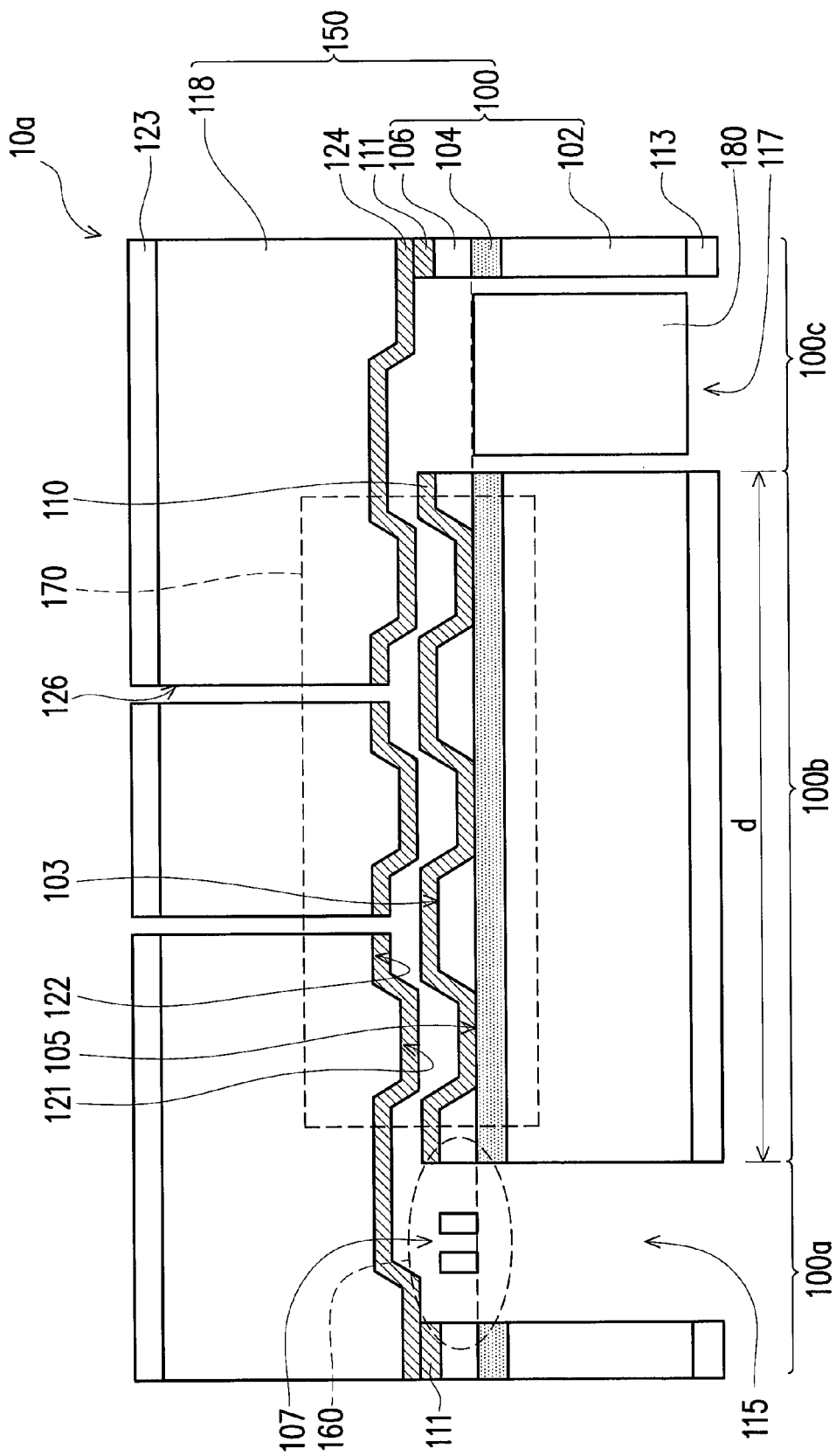

Referring to FIG. 2H, the first sub-substrate 100 is bonded to the second sub-substrate 118, wherein the convex portions 103 of the first sub-substrate 100 correspond to the concave portions 122 of the second sub-substrate 118, and the concave portions 105 of the first sub-substrate 100 correspond to the convex portions 121 of the second sub-substrate 118. In an embodiment, the first sub-substrate 100 is bonded to the second sub-substrate 118 with a joint component 130, as shown in FIG. 2H. The joint component 130 can be, but is not limited to, adhesive, conductive glue or metal. In another embodiment, the first sub-substrate 100 is directly bonded to the second sub-substrate 118 without using a joint component, as shown in the optical gas sensor 10a of FIG. 2H-1.

A light detector 180 is inserted into the opening 117 of the first sub-substrate 100 to complete the fabrication of the optical gas sensor 10 of the first embodiment. The optical gas sensor 10 is a wafer-level integrated platform, in which the light source 160, the reaction chamber structure 170 and the light detector 180 can be effectively integrated together.

In the said embodiment, the light source 160 can be formed simultaneously during the step of forming the reaction chamber structure 170. However, the application is not limited thereto. People skilled in the art should appreciate that a commercially available light source can be purchased upon the customer requirement, and such light source can be inserted into the first area 100a of the substrate 150.

The said embodiment in which the reaction chamber structure is formed by the first and second sub-substrates having different materials is provided for illustration purposes, and is not construed as limiting the application. The reaction chamber structure can be formed by the first and second sub-substrates having the same material. For example, convex portions and concave portions of each of two metal substrates are fabricated by the imprint technology, and the two metal substrates are then bonded to each other correspondingly. In another embodiment, convex portions and concave portions of each of two plastic substrates are fabricated by the injection moulding technology, and the two plastic substrates are then bonded to each other correspondingly. People skilled in the art should appreciate that, without departing from the scope of the application, the reaction chamber structure of the application can be formed by any known technology with any substrate material, as long as the shortest travel distance of the light in the reaction chamber structure is greater than the straight-line distance from the light source to the light detector.

Second Embodiment

Figure 3A:
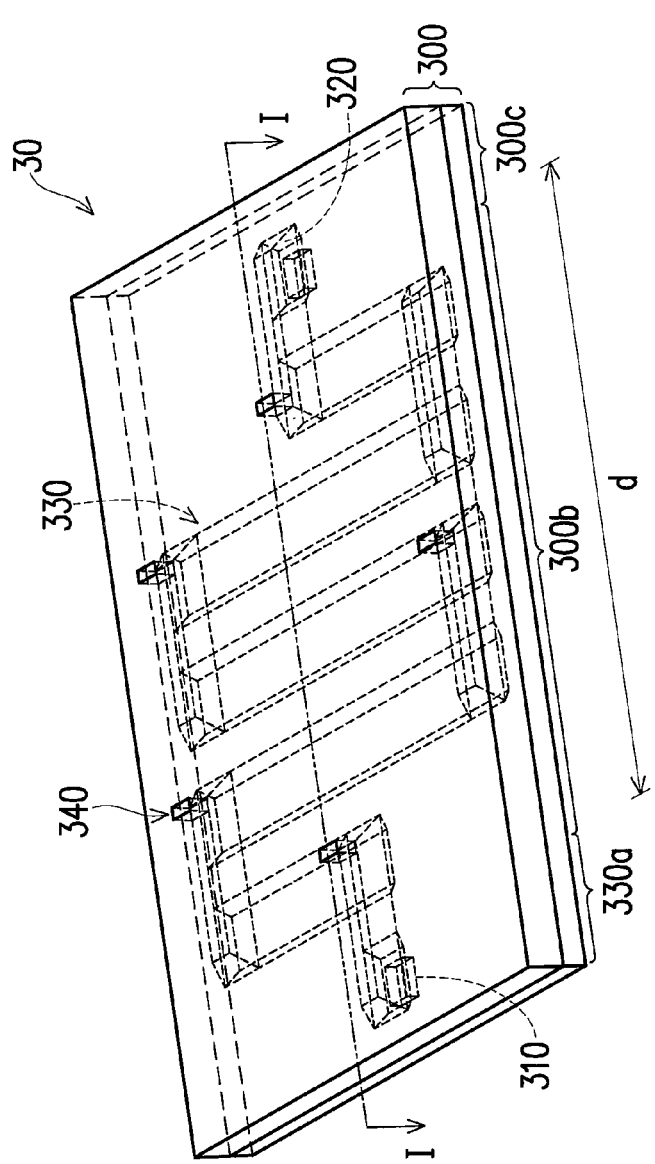
FIG. 3A is a three-dimensional schematic diagram illustrating an optical gas sensor according to the second embodiment.
Figure 3B:
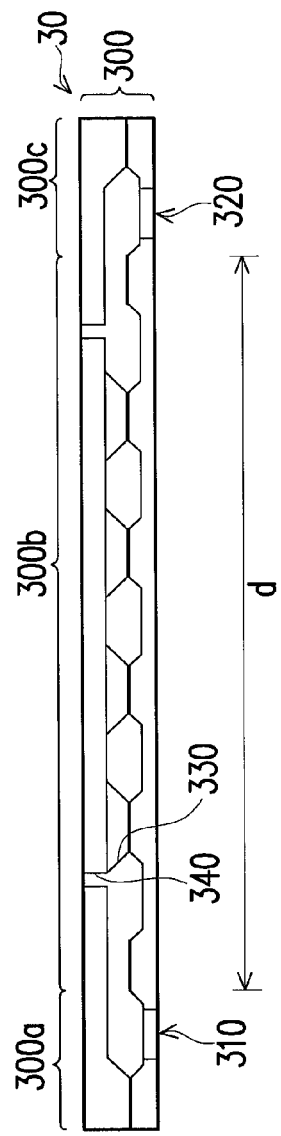
FIG. 3B is a cross-sectional schematic diagram taken along line I-I of FIG. 3A.

FIG. 3A is a three-dimensional schematic diagram illustrating an optical gas sensor according to the second embodiment. FIG. 3B is a cross-sectional schematic diagram taken along line I-I of FIG. 3A.

Referring to FIGS. 3A and 3B, the optical gas sensor 30 of the second embodiment includes a substrate 300, a light source 310, a light detector 320, a reaction chamber structure 330 and a plurality of gas holes 340.

The substrate 300 has a first area 300a, a second area 300b and a third area 300c. The second area 300b is disposed between the first area 300a and the third area 300c. In an embodiment, the first area 300a is a light source area, the second area 300b is a reaction chamber area, and the third area 300c is a light detector area.

The light source 310, the light detector 320 and the reaction chamber structure 330 are separately disposed in the substrate 300. The reaction chamber structure 330 is connected between the light source 310 and the light detector 320, and a reflective layer (not shown) can be coated on the inner wall thereof. In addition, the gas holes 340 for gas in and out are disposed in the substrate 300 and in communication with the reaction chamber structure 330.

It is noted that in the second embodiment, the reaction chamber structure 330 has a serpentine shape, so that the shortest travel path of the light in the reaction chamber structure 330 is greater than the straight-line distance d from the light source 310 to the light detector 320. Accordingly, the light reflection path is increased and the performance of the gas sensor is enhanced.

Third Embodiment

Figures 4A, 4B:
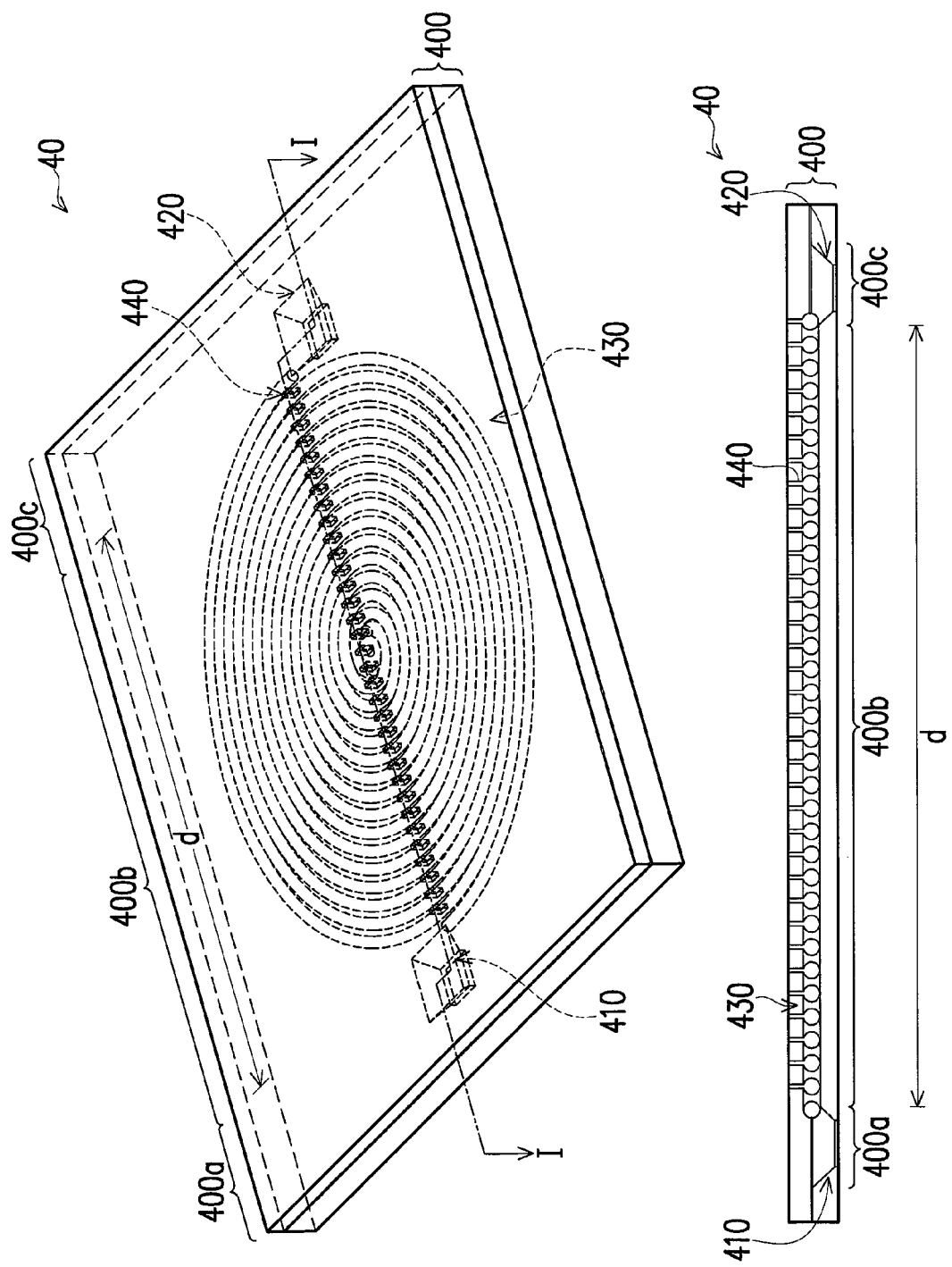
FIG. 4A is a three-dimensional schematic diagram illustrating an optical gas sensor according to the third embodiment.
FIG. 4B is a cross-sectional schematic diagram taken along line I-I of FIG. 4A.

FIG. 4A is a three-dimensional schematic diagram illustrating an optical gas sensor according to the third embodiment. FIG. 4B is a cross-sectional schematic diagram taken along line I-I of FIG. 4A.

Referring to FIGS. 4A and 4B, the optical gas sensor 40 of the third embodiment includes a substrate 400, a light source 410, a light detector 420, a reaction chamber structure 430 and a plurality of gas holes 440.

The substrate 400 has a first area 400a, a second area 400b and a third area 400c. The second area 400b is disposed between the first area 400a and the third area 400c. In an embodiment, the first area 400a is a light source area, the second area 400b is a reaction chamber area, and the third area 400c is a light detector area.

The light source 410, the light detector 420 and the reaction chamber structure 430 are separately disposed in the substrate 400. The reaction chamber structure 430 is connected between the light source 410 and the light detector 420, and a reflective layer (not shown) can be coated on the inner wall thereof. In addition, the gas holes 440 for gas in and out are disposed in the substrate 400 and in communication with the reaction chamber structure 430.

It is noted that in the third embodiment, the reaction chamber structure 330 has a spiral shape, so that the shortest travel path of the light in the reaction chamber structure 430 is greater than the straight-line distance d from the light source 410 to the light detector 420. Accordingly, the light reflection path is increased and the performance of the gas sensor is enhanced.

Fourth Embodiment

Figures 5A, 5B:
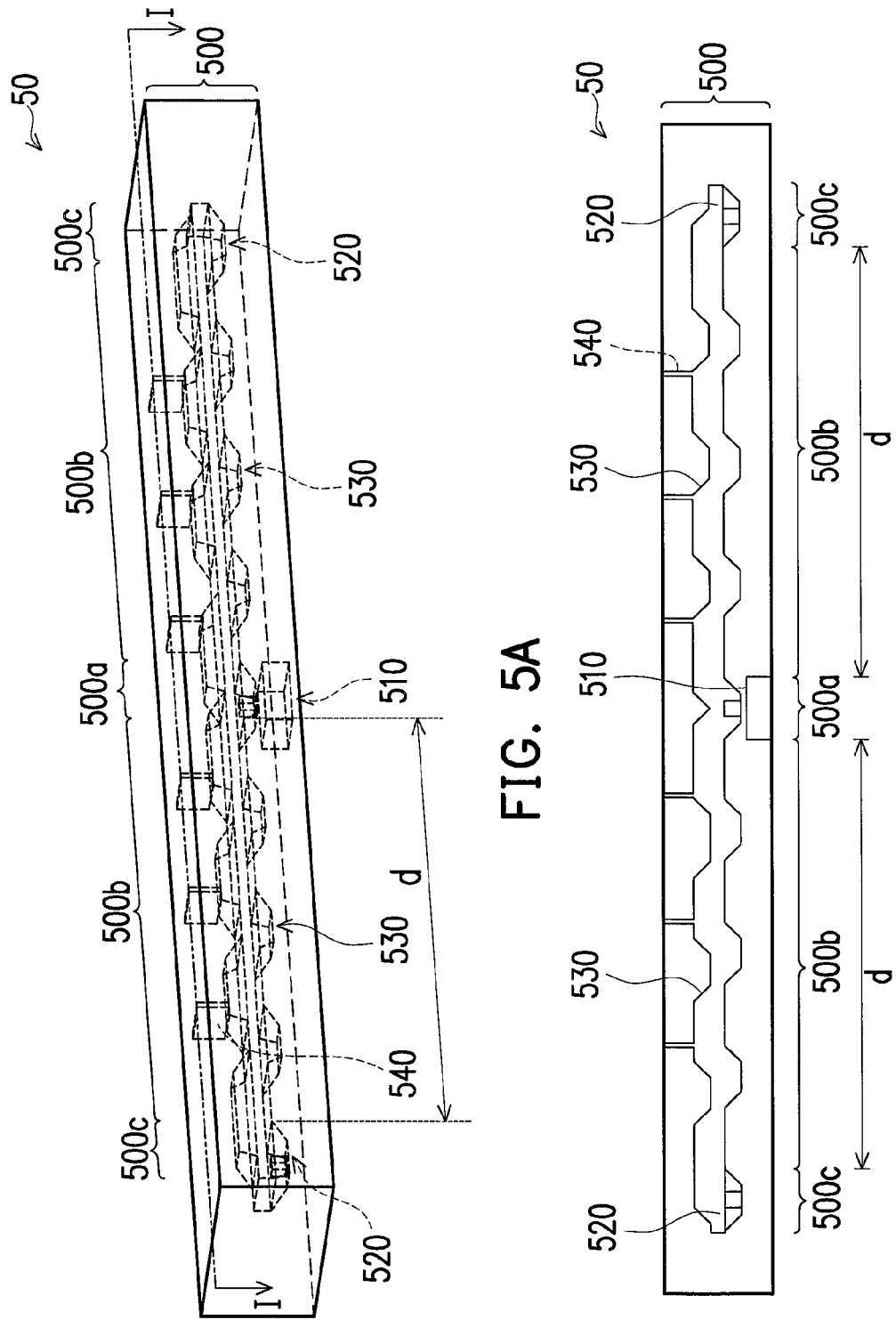
FIG. 5A is a three-dimensional schematic diagram illustrating an optical gas sensor according to the fourth embodiment.
FIG. 5B is a cross-sectional schematic diagram taken along line I-I of FIG. 5A.

FIG. 5A is a three-dimensional schematic diagram illustrating an optical gas sensor according to the fourth embodiment. FIG. 5B is a cross-sectional schematic diagram taken along line I-I of FIG. 5A.

Referring to FIGS. 5A and 5B, the optical gas sensor 50 of the fourth embodiment includes a substrate 500, a light source 510, two light detectors 520, two reaction chamber structures 530 and a plurality of gas holes 540.

The substrate 500 has a first area 500a, two second areas 500b and two third areas 500c. Each second area 500b is disposed between the first area 500a and the corresponding third area 500c. In an embodiment, the first area 500a is a light source area, each second area 500b is a reaction chamber area, and each third area 500c is a light detector area.

The light source 510, the light detectors 520 and the reaction chamber structures 530 are separately disposed in the substrate 500. When two light detectors 520 are provided, two light detectors 520 are disposed at the opposite sides of the light source 510. Each reaction chamber structure 530 is located between the light source 510 and the corresponding light detector 520, and a reflective layer (not shown) can be coated on the inner wall thereof. In addition, the gas holes 540 for gas in and out are disposed in the substrate 500 and in communication with the reaction chamber structure 530.

In this embodiments, two light detectors 520 are disposed at the opposite sides of the light source 510, but the application is not limited thereto. In another embodiment, two light detectors 520 can located at any two locations of the light source 510.

It is noted that the reaction chamber structure of the fourth embodiment has a similar configuration to that of the first embodiment. Similarly, the shortest travel path L of the light in the reaction chamber structure 530 is greater than the straight-line distance d from the light source 510 to the light detector 520, so that the light reflection path is increased and the performance of the gas sensor is enhanced. Further, since the optical gas sensor 50 of the fourth embodiment has two light detectors 520 and two reaction chamber structures 530, two light signals can be detected simultaneously. That is, two or more gases can be detected at the same time so as to broaden the application of the optical gas sensor of the application.

Each of the reaction chamber structures in the third and fourth embodiments is designed in a 2D configuration, and the light travel path is at the same plane turning horizontally but not turning up and down. However, the application is not limited thereto. People skilled in the art should appreciate that each of the reaction chamber structures in the third and fourth embodiments can be designed in a 3D configuration, in which convex portions and concave portions as described in the first embodiment are further included to increase the light reflection path.

Fifth Embodiment

Figure 6:
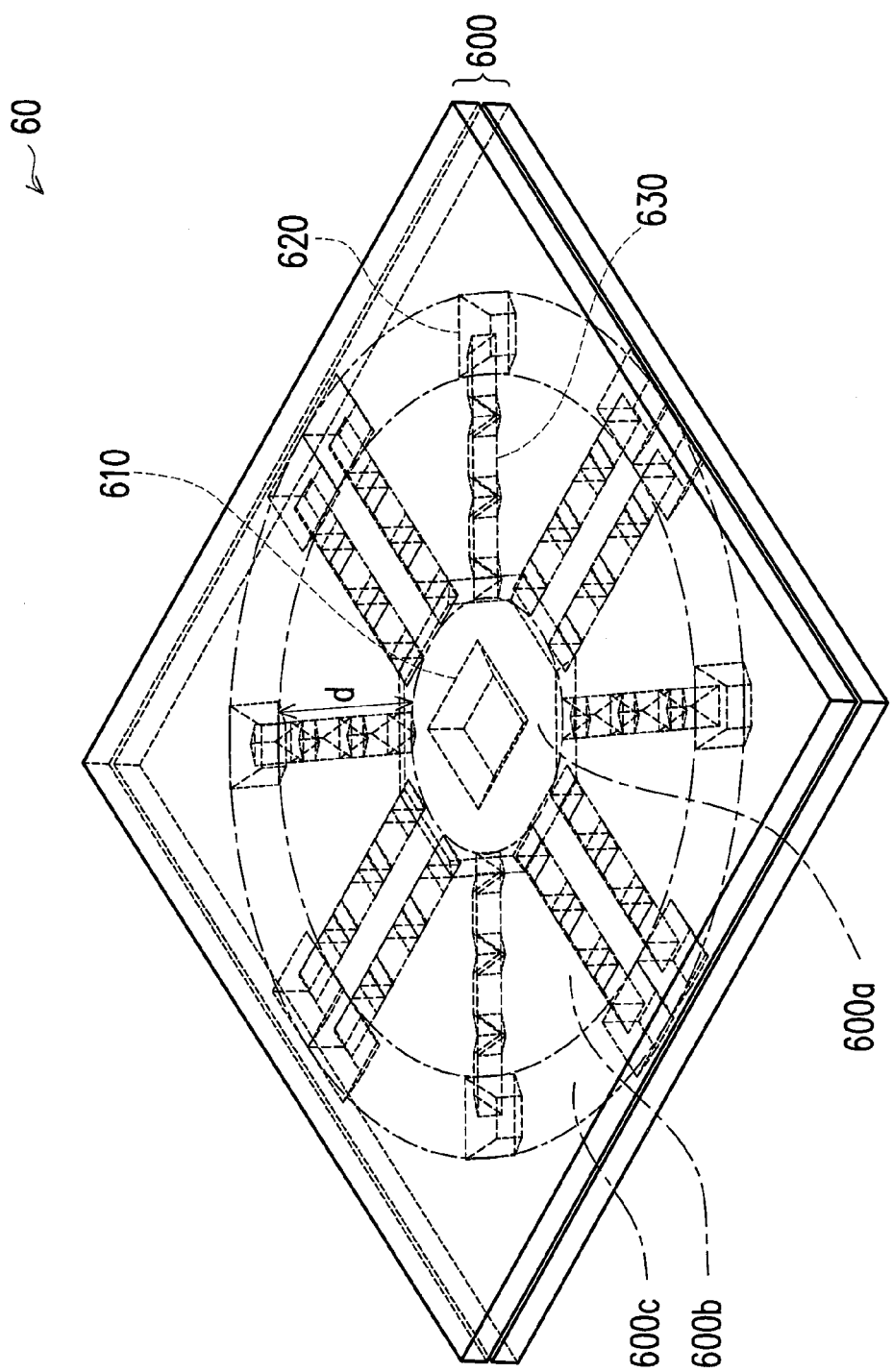
FIG. 6 is a three-dimensional schematic diagram illustrating an optical gas sensor according to the fifth embodiment.

FIG. 6A is a three-dimensional schematic diagram illustrating an optical gas sensor according to the fifth embodiment.

Referring to FIG. 6A, the optical gas sensor 60 of the fifth embodiment includes a substrate 600, a light source 610, a plurality of light detectors 620 and a plurality of reaction chamber structures 630.

This embodiment in which the optical gas sensor 60 has twelve light detectors 620 and twelve reaction chamber structures 630 is provided for illustration purposes, and is not construed as limiting the application. In other words, the number of the light detectors and reaction chamber structures is not limited by the application.

The substrate 600 has a first area 600a, a second area 600b and a third area 600c. The second area 600b is disposed between the first area 600a and the third area 600c. Specifically, the third area 600c surrounds the second area 600b, and the second area 600b surrounds the first area 600a. In an embodiment, the first area 600a is a light source area, the second area 600b is a reaction chamber area, and the third area 600c is a light detector area.

The light source 610, the light detector 6520 and the reaction chamber structure 630 are separately disposed in the substrate 600. The reaction chamber structures 630 are radially arranged from the light source 610 as a center. Each reaction chamber structure 630 is located between the light source 610 and the corresponding light detector 620, and a reflective layer (not shown) can be coated on the inner wall thereof. In addition, a plurality of gas holes (not shown) for gas in and out are disposed in the substrate 600 and in communication with the reaction chamber structure 630.

It is noted that the reaction chamber structure of the fifth embodiment has a similar configuration to that of the first embodiment. Similarly, the shortest travel path L of the light in the reaction chamber structure 630 is greater than the straight-line distance d from the light source 610 to the light detector 620, so that the light reflection path is increased and the performance of the gas sensor is enhanced. Further, since the optical gas sensor 60 of the fifth embodiment has twelve light detectors 620 and twelve reaction chamber structures 630, twelve light signals can be detected simultaneously. That is, twelve or more gases can be detected at the same time so as to broaden the application of the optical gas sensor of the application.

A computer simulation testing is proceeded to prove the performance of the application. A chip has dimensions of 10×4×1 mm$^3$ (L×W×H) is provided. A reaction chamber structure is designed in the chip, and a light source and a light detector are disposed beside the reaction chamber structure (i.e. chip). The reaction chamber structure similar to that of FIG. 1A has eight sub-chambers, each of which is composed of a convex portion and a corresponding concave portion. Each sub-chamber has dimensions of 1.35×2.6×0.25 mm$^3$ (L×W×H). Sixteen gas holes are in communication with the reaction chamber structure. The light is reflected many times and enters the light detector. The average light path in such optical gas sensor chip is about 27.6 mm, which is much greater than 10 mm of the chip length. Accordingly, the structure of the application is proved to enhance the light reflection path.

In summary, in the optical gas sensor of the application, a three-dimensional reaction chamber structure is used to replace the traditional simple structure, so that the performance of the gas sensor can be enhanced in a wafer-level size. Besides, a light source, a reaction chamber and a light detector are integrated into one wafer so as to achieve the wafer-level integration, wherein high specificity for the gas to be detected, excellent gas identification, small volume and reduced cost can be easily realized with such optical gas sensor. In addition, the optical gas sensor of the application can detect various gases simultaneously and has wide application in fields such as home environment monitoring, industrial safety, and disease diagnosis and treatment.

It will be apparent to those skilled in the art that various modifications and variations can be made to the structure of the disclosed embodiments without departing from the scope or spirit. In view of the foregoing, it is intended that the disclosure cover modifications and variations of this disclosure provided they fall within the scope of the following claims and their equivalents.

What is claimed is:

1. An optical gas sensor, comprising:
    a substrate;
    a light source, disposed in the substrate;
    at least one light detector, disposed in the substrate; and
    at least one reaction chamber structure, disposed in the substrate and connected between the light source and the light detector,
    wherein the distance from the light source to the light detector is d, and a shortest travel path of a light from the light source to the light detector through the reaction chamber structure is greater than d,
    wherein the at least one reaction chamber structure is composed of a first sub-substrate and a second sub-substrate, the first sub-substrate has a plurality of convex portions and concave portions disposed alternately, the second sub-substrate has a plurality of convex portions and concave portions disposed alternately, and
    wherein the convex portions of the first sub-substrate correspond to the concave portions of the second sub-substrate, and the concave portions of the first sub-substrate correspond to the convex portions of the second sub-substrate.

2. The optical gas sensor of claim 1, wherein the substrate comprises a silicon-on-insulator (SOI) substrate, a silicon substrate, a metal substrate, a plastic substrate or a combination thereof.

3. The optical gas sensor of claim 1, wherein a material of the first sub-substrate is the same as a material of the second sub-substrate.

4. The optical gas sensor of claim 1, wherein a material of the first sub-substrate is different from a material of the second sub-substrate.

5. The optical gas sensor of claim 1, wherein a reflective layer is coated on an inner wall of the reaction chamber structure.

6. The optical gas sensor of claim 1, further comprising a plurality of gas holes for gas in and out, the gas holes disposed in the substrate and in communication with the reaction chamber structure.

7. The optical gas sensor of claim 1, wherein the reaction chamber structure has a serpentine shape.

8. The optical gas sensor of claim 1, wherein the reaction chamber structure has a spiral shape.

9. The optical gas sensor of claim 1, wherein the optical gas sensor is a wafer-level gas optical gas sensor.

10. The optical gas sensor of claim 1, wherein a number of the at least one light detector is more than one, a number of the at least one reaction chamber structure is more than one, and each of the reaction chamber structures is located between the light source and the corresponding light detector.

11. The optical gas sensor of claim 10, wherein the reaction chamber structures are radially arranged from the light source as a center.

* * * * *